(12) United States Patent
Rambach

(10) Patent No.: US 7,198,907 B2
(45) Date of Patent: Apr. 3, 2007

(54) VIBRIO BACTERIA DETECTION AND DIFFERENTIATION

(76) Inventor: Alain Rambach, 73, Boulevard Montparnasse, 75006 Paris (FR)

( * ) Notice: Subject to any disclaimer, the term of this patent is extended or adjusted under 35 U.S.C. 154(b) by 154 days.

(21) Appl. No.: 10/311,875

(22) PCT Filed: Jun. 27, 2001

(86) PCT No.: PCT/FR01/02033

§ 371 (c)(1),
(2), (4) Date: Feb. 26, 2003

(87) PCT Pub. No.: WO02/00922

PCT Pub. Date: Jan. 3, 2002

(65) Prior Publication Data

US 2004/0265946 A1     Dec. 30, 2004

(30) Foreign Application Priority Data

Jun. 27, 2000   (FR)   .................... 00 08237

(51) Int. Cl.
*C12Q 1/04*   (2006.01)
(52) U.S. Cl. .................. 435/34; 435/243; 435/253.6
(58) Field of Classification Search .................. 435/34, 435/243, 253.6
See application file for complete search history.

(56) References Cited

U.S. PATENT DOCUMENTS

| | | | | |
|---|---|---|---|---|
| 5,364,767 A | * | 11/1994 | Flowers et al. | 435/39 |
| 6,008,008 A | * | 12/1999 | James et al. | 435/34 |
| 6,130,057 A | * | 10/2000 | Gosnell et al. | 435/32 |
| 6,350,588 B1 | * | 2/2002 | Roth et al. | 435/34 |

FOREIGN PATENT DOCUMENTS

JP   2001008679 A   *   1/2001

OTHER PUBLICATIONS

Kilian et al. Rapid diagnosis of Enterobacteriaceae. I. Detection of bacterial glycosidases. (1976) Acta path. microbiol. scand. Sect. B. 84B(5):pp. 245-251.*
O'Brien et al. Modified taurocholate-tellurite-gelatin agar for improved differentiation of Vibrio species. (1985) Journal of clinical microbiology. 22(6):pp. 1011-1013.*
Fujiwara et al. A selective medium for the isolation of *Vibrio parahaemolyticus*. II. BTB-TTGA agar medium. (1965) Shokuhin Eiseigaku Zasshi. 6(5):pp. 437-439. CAPLUS abstract.*
Labrousse et al. Miniaturization of beta-galactosidase immunoassays using chromogenic and flurorgenic substrates. (1982) Journal of Immunological Methods. 48(2):pp. 133-147. CAPLUS abstract.*
Atlas, RM. Handbook of Microbiological Media, $2^{nd}$ ed. 1997. CRC Press, Inc. p. 1351.*
Armon, R et al. A modified m-CP medium for enumerating *Clostridium perfringens* from water samples. Can. J. Microbiol. 1988. 34: 78-79.*
O'Brien et al., "Modified Taurocholate-Tellurite-Gelatin Agar for Improved Differentiation of Vibro Species", Journal of Clinical Mirobiology, vol. 22, No. 6, 1985, pp. 1011-1013.
Chang et al., "Development of a Latex Agglultination Test for the Rapid Identification of *Vibrio parahaemolyticus*", Journal of Food Protection, vol. 57, No. 1, 1994, pp. 31-36.
Chatterjee et al., "Studies of the Beta D Galactosidase Activity of *Vibrio-parhaemolyticus*" Indian Journal of Medical Research, vol. 60, No. 6, 1972, pp. 831-833.
Bhattacharya et al., "Studies of Beta Galactosidase Activity in Vibro-Eitor", Canadian Journal of Microbiology, vol. 20, No. 6, 1974, pp. 897-898.
Maugeri et al., "Potentially Pathogenic Vibrios in Brackish Waters and Mussels.", Journal of Applied Microbiology, vol. 89, No. 2, pp. 261-266, 2000.

* cited by examiner

*Primary Examiner*—Leon B. Lankford, Jr.
*Assistant Examiner*—Susan E. Fernandez
(74) *Attorney, Agent, or Firm*—Heller Ehrman LLP

(57) ABSTRACT

The invention concerns a culture medium for isolating *Vibrio* bacteria, characterised in that it comprises, in a *Vibrio* culture medium, at least a chromogenic agent selected among the β-glucosidase substrates and the β-galactosidase substrates.

11 Claims, No Drawings

VIBRIO BACTERIA DETECTION AND DIFFERENTIATION

The present invention relates to a chromogenic culture medium intended to reveal bacteria of the *Vibrio* genus.

The *Vibrio* genus is associated with cholera (*V. cholerae*) and with several other clinical pathologies. In particular, *V. parahaemolyticus* is responsible for certain types of acute gastroenteritis, in particular in Japan, observed after ingesting contaminated food (generally products from the sea, fish, shellfish, crustacia or molluscs which are raw or only slightly cooked).

Transmission of the *cholera vibrio* generally takes place from human to human (vomit, fecal matter, sweat), or via contaminated foods. Moreover, *vibrios* are naturally found in the microbial flora of coastal and estuary waters. Included among their natural hosts are molluscs, crustacia, fish, echinoderms and plankton.

*Vibrio* infections pose a public health problem, and it is therefore important to have a reliable and rapid test for detecting food contaminations by these bacteria.

There exist today reasonably selective culture media which make it possible to detect the presence of *vibrios* in samples. In particular, use is made of TCBS agar (sodium Thiosulfate—sodium Citrate—bovine Bile—Sucrose) (Diagnostics Pasteur, ref. 69456; Oxoid, ref. CM 333; Merck, ref. 10263). The vast majority of enterobacteria and enterococci grow very little, or not at all, on this medium compared to *vibrios*.

TTG agar (Taurocholate—Tellurite—Gelatin) is also used, but is relatively tedious to prepare, requiring regular controls and rigorous dosing of the potassium tellurite.

One of the drawbacks of the TCBS medium is that it does not generally make it possible to differentiate between the various species of *vibrios*. It would in fact be advisable to be able to identify the species of *Vibrio* present in the sample analyzed. In particular, it would be advantageous to be able to identify the presence of and to differentiate *V. cholerae*, *V. parahaemolyticus*, and *V. alginolyticus*. The latter species is only rarely associated with diarrhoea producing pathologies, but is probably the entity most frequently isolated in countries with a temperate climate, in a large diversity of clinical samples.

In order to improve the health risk evaluation, it is therefore advisable to be able to differentiate the various types of *vibrios* which may be present in samples (food samples, feces, etc.), more finely than that which was obtained with the preceding media, which could only differentiate sucrose$^+$ bacteria (such as *V. alginolyticus* or *V. cholerae*) for sucrose$^-$ bacteria (such as *V. parahaemolyticus*).

The present invention proposes to provide a novel culture medium for detecting and/or differentiating bacteria of the *Vibrio* genus, characterized in that it comprises, in a *Vibrio* culture medium, at least one chromogenic agent chosen from β-glucosidase substrates and β-galactosidase substrates.

The chromogenic agent which is a substrate for one of the enzymes mentioned above comprises a chromophore, which is released by hydrolysis of the substrate by its enzyme. Thus, the bacterial colony becomes colored according to the chromophore released.

Said chromophore is preferably chosen from indoxyl, haloindoxyl (bromoindoxyl, chloroindoxyl, fluoroindoxyl, iodoindoxyl, dichloroindoxyl, chlorobromoindoxyl, trichloroindoxyl), methylindoxyl or hydroxyquinoline derivatives. Preferred derivatives are in particular chosen from the following derivatives: 6-chloroindoxyl, 5-bromoindoxyl, 3-bromoindoxyl, 6-fluoroindoxyl, 5-iodoindoxyl, 4,6-dichloroindoxyl, 6,7-dichloroindoxyl, 5-bromo-4-chloroindoxyl, 5-bromo-6-chloroindoxyl, 4,6,7-trichloroindoxyl, N-methylindoxyl and 8-hydroxyquinoline.

Thus, preferably the β-glucosidase substrate is an indoxyl glucoside, and/or the β-galactosidase substrate is an indoxyl galactoside.

The concentration of each chromogenic agent in the medium is between approximately 0.02 and 0.5 g/l. A preferred concentration is 0.1 g/l.

*V. parahaemolyticus* is described as being negative for the β-glucosidase characteristic (Rapid 20E identification gallery from the company BioMérieux, Marcy l'Etoile, France), and as being positive for the β-galactosidase characteristic (API 20 NE identification gallery from the company BioMérieux mentioned above).

Surprisingly, the invention shows that *V. parahaemolyticus* can exhibit a reverse phenotype for these two characteristics on solid medium. Thus, the use of a chromogenic agent which is a substrate for β-glucosidase makes it possible to color the colonies on solid medium, whereas they remain colorless when a chromogenic agent which is a substrate for β-galactosidase is used.

It is, however, difficult to distinguish and differentiate *V. parahaemolyticus* from *V. alginolyticus*, which are often found in the same samples of marine origin, since these two species have many common characteristics. Thus, the two species are both positive for the β-glucosidase characteristic. Surprisingly, the addition of sucrose to the medium according to the invention, in particular at a high concentration, makes it possible to cause the β-glucosidase activity of *V. alginolyticus* to disappear, while at the same time allowing it to remain in *V. parahaemolyticus*. Thus, the medium according to the invention makes it possible to readily distinguish between *V. parahaemolyticus* and *V. alginolyticus*, by simple coloration or lack of coloration of the colonies present on the culture medium.

A high concentration of sucrose should be considered to be a sucrose concentration greater than 5 g/l, preferably between 5 g/l and 35 g/l. An effective sucrose concentration is 20 g/l.

The present invention also makes it possible to detect *V. cholerae*, and to differentiate it with respect to the other two species mentioned above. Specifically, *V. cholerae* exhibits β-galactosidase activity without exhibiting β-glucosidase activity. Thus, the addition of a chromogenic agent which is a substrate for β-galactosidase, to a *Vibrio* culture medium, makes it possible to distinguish *V. cholerae* from the other *vibrios*, by coloration of the colonies formed.

In order to be able to differentiate the various bacteria in a single step, it is therefore advantageous to use a culture medium which comprises both a chromogenic agent which is a substrate for β-galactosidase and a chromogenic agent which is a substrate for β-glucosidase.

In fact, addition of sucrose to the culture medium does not cause the β-galactosidase characteristic of *V. cholerae* to disappear. This result is all the more surprising since an inhibition is observed for *V. alginolyticus*, which exhibits the same sucrose$^+$ characteristic as *V. cholerae*.

Thus, the use of a culture medium comprising both a chromogenic agent which is the substrate for β-galactosidase and a chromogenic agent which is a substrate for β-glucosidase makes it possible to differentiate *V. parahaemolyticus* (mauve when 5-bromo-6-chloro-3-indoxyl-β-glucoside is used), *V. cholerae* (blue when 5-bromo-4-chloro-3-indoxyl-β-galactoside is used) and *V. alginolyticus*

(colorless). Such a medium according to the invention therefore makes it possible to detect and differentiate three different strains of *vibrios*, whereas the media of the prior art only make it possible to obtain a two-category differentiation (sucrose⁺ and sucrose⁻).

The present invention is also directed toward a method for detecting and/or differentiating bacteria of the *Vibrio* genus in a sample, characterized in that it comprises the following steps:
a. inoculating a culture medium according to the invention with said sample or an inoculum derived from the sample,
b. detecting the presence of bacteria of the *Vibrio* genus on said culture medium,
c. optionally, differentiating *V. cholerae, V. parahaemolyticus* and *V. alginolyticus* present on said culture medium.

The use of these media is generally preceded by an enrichment step, using methods known to those skilled in the art. Alkaline peptone water containing 1 g % of NaCl (pH 8.6) or alkaline peptone water containing 3 g % of NaCl may in particular be used.

Diverse selective factors for *Vibrio*, which are well known to those skilled in the art, may be added to the medium of the present invention. Thus, the presence of an alkaline pH, of thiosulfate, of citrate, of bile, or biliary salt, of magnesium, of calcium, of teepol, of SDS, of Polyximine, of colistine, of tellurite, etc. makes it possible to improve the properties of the medium according to the invention, and to isolate the *Vibrios* in a satisfactory manner.

EXAMPLES

Example 1

A preferred medium for use of the invention comprises (per liter):

| | |
|---|---|
| Agar | 15 g |
| Peptone | 15 g |
| Yeast extract | 3 g |
| NaCl | 10 g |
| 5-Bromo-6-chloro-3-indoxyl-β-glucoside | 0.1 g |
| 5-Bromo-4-chloro-3-indoxyl-β-galactoside | 0.1 g |
| Sucrose | 20 g |
| Glucose | 1 g |
| Lactose | 0.1 g |
| IPTG | 0.04 g |
| Trizma base | 5 g |
| Sodium citrate | 10 g |
| Sodium thiosulfate | 10 g |
| Sodium cholate | 3 g |

Example 2

Plating bacteria out on various media gave the following results.

| | TCBS | BTB-Teepol | Medium of the invention (Example 1) |
|---|---|---|---|
| *V. cholerae* | Yellow | Yellow | Blue |
| *V. alginolyticus* | Yellow | Yellow | Colorless |
| *V. parahaemolyticus* | Green | Blue-green | Mauve |

The use of the medium according to the invention thus makes it possible to differentiate the three species of vibrios, compared to the media of the prior art.

The invention claimed is:
1. A culture medium comprising (per liter);

| | |
|---|---|
| Agar | 15 g |
| Peptone | 15 g |
| Yeast extract | 3 g |
| NaCl | 10 g |
| 5-Bromo-6-chloro-3-indoxyl-β-glucoside | 0.1 g |
| 5-Bromo-4-chloro-3-indoxyl-β-galactoside | 0.1 g |
| Sucrose | 20 g |
| Glucose | 1 g |
| Lactose | 0.1 g |
| IPTG | 0.04 g |
| Trizma base | 5 g |
| Sodium citrate | 10 g |
| Sodium thiosulfate | 10 g |
| Sodium cholate | 3 g. |

2. A method for differentiating *V. parahaemolyticus* from *V. alginolyticus* in a sample of bacteria of the *Vibrio* genus, comprising the following steps:
a. inoculating a *Vibrio* culture medium comprising at least one chromogenic agent that is a substrate for β-glucosidase and sucrose at a concentration of greater than 5 g/l with a sample of bacteria of the *Vibrio* genus or an inoculum derived from said sample, and
b. detecting enzyme activity for *V. parahaemolyticus* and an absence of β-glucosidase activity for *V. alginolyticus* in said culture medium, thereby differentiating *V. parahaemolyticus* from *V. alginolyticus*.

3. The method of claim 2, wherein in said *Vibrio* culture medium, said at least one chromogenic agent releases, by hydrolysis, a chromophore selected from the group consisting of an indoxyl, haloindoxyl, methylindoxyl and hydroxyquinoline.

4. The method of claim 2, wherein in said *Vibrio* culture medium said β-glucosidase substrate is indoxyl glucoside.

5. The method of claim 4, wherein said β-glucosidase substrate is 5-bromo-6-chloro-3-indoxyl-β-glucoside.

6. The method of claim 2, wherein said *Vibrio* culture medium further comprises a β-galactosidase substrate that is indoxyl galactoside.

7. The method of claim 2, wherein said *Vibrio* culture medium further comprises a β-galactosidase substrate that is 5-bromo-4-chloro-3-indoxyl-β-galactoside.

8. The method of claim 3, wherein said haloindoxyl is selected from the group consisting of bromoindoxyl, chloroindoxyl, fluoroindoxyl, iodoindoxyl, dichloroindoxyl, chlorobromoindoxyl, and trichloroindoxyl.

9. The method of claim 8, wherein said haloindoxyl is selected from the group consisting of: 6-chloroindoxyl, 5-bromoindoxyl, 3-bromoindoxyl, 6-fluoroindoxyl, 5-iodoindoxyl, 4,6-dichloroindoxyl, 6,7-dichloroindoxyl, 5-bromo-4-chloroindoxyl, 5-bromo-6-chloroindoxyl and 4,6,7-trichloroindoxyl.

10. The method of claim 3, wherein said hydroxyquinoline is 8-hydroxyquinoline.

11. The method of claim 3, wherein said methylindoxyl is N-methylindoxyl.

\* \* \* \* \*